United States Patent
Ajiki

(10) Patent No.: US 10,010,267 B2
(45) Date of Patent: Jul. 3, 2018

(54) MASSAGE MEASUREMENT APPARATUS AND MASSAGE MEASUREMENT METHOD

(71) Applicant: Panasonic Intellectual Property Management Co., Ltd., Osaka (JP)

(72) Inventor: Kaori Ajiki, Osaka (JP)

(73) Assignee: PANASONIC INTELLCTUAL PROPERTY MANAGEMENT CO., LTD., Osaka (JP)

(*) Notice: Subject to any disclaimer, the term of this patent is extended or adjusted under 35 U.S.C. 154(b) by 667 days.

(21) Appl. No.: 14/633,471

(22) Filed: Feb. 27, 2015

(65) Prior Publication Data
US 2015/0257677 A1 Sep. 17, 2015

(30) Foreign Application Priority Data
Mar. 13, 2014 (JP) .................. 2014-049837

(51) Int. Cl.
- *A61B 5/103* (2006.01)
- *A61B 5/00* (2006.01)
- *A61H 37/00* (2006.01)

(52) U.S. Cl.
CPC .......... *A61B 5/1036* (2013.01); *A61B 5/6803* (2013.01); *A61B 5/6814* (2013.01);
(Continued)

(58) Field of Classification Search
CPC ................ A61H 37/00; A61H 2230/50; A61H 2201/0184; A61H 2230/25; A61H 2205/022; A61H 2201/5061; A61H 2201/501; A61H 2201/1654; A61B 5/1036; A61B 5/6821; A61B 5/6814; A61B 5/6803; A61B 2560/0425; A61B 2562/0247; A61B 2562/046
See application file for complete search history.

(56) References Cited

U.S. PATENT DOCUMENTS 5,396,881 A * 3/1995 Klein .................. A61B 5/0492
2/206
2007/0257256 A1 11/2007 Kugler
(Continued)

FOREIGN PATENT DOCUMENTS

| JP | 11-118635 | 4/1999 |
| JP | 2004-132765 A | 4/2004 |

(Continued)

OTHER PUBLICATIONS

The Extended European Search Report dated Jul. 16, 2015 for the related European Patent Application No. 15157269.0.
(Continued)

*Primary Examiner* — Rene Towa
(74) *Attorney, Agent, or Firm* — Greenblum & Bernstein, P.L.C.

(57) ABSTRACT

A massage measurement apparatus includes a sheet member attachable to a skin of a body, and a measurement unit that measures a pressure distribution on the sheet member, wherein the sheet member has an indication that indicates an area of the skin, to which the sheet member is to be attached, and wherein the measurement unit measures the pressure distribution with reference to one or more positions on the body in a state in which the sheet member is attached to the skin.

10 Claims, 12 Drawing Sheets

(52) U.S. Cl.
CPC .......... *A61B 5/6821* (2013.01); *A61H 37/00* (2013.01); *A61B 2560/0425* (2013.01); *A61B 2562/0247* (2013.01); *A61B 2562/046* (2013.01); *A61H 2201/0184* (2013.01); *A61H 2201/1654* (2013.01); *A61H 2201/501* (2013.01); *A61H 2201/5061* (2013.01); *A61H 2205/022* (2013.01); *A61H 2230/25* (2013.01); *A61H 2230/50* (2013.01)

(56) References Cited

U.S. PATENT DOCUMENTS

| | | |
|---|---|---|
| 2009/0058274 A1 | 3/2009 | Yokoyama et al. |
| 2010/0305484 A1 | 12/2010 | Grollier et al. |
| 2013/0158451 A1 | 6/2013 | Juto et al. |
| 2014/0142477 A1* | 5/2014 | Park ................. A61H 23/02 601/46 |
| 2014/0163385 A1* | 6/2014 | Kelleher ............ A61B 5/0059 600/473 |
| 2014/0257073 A1* | 9/2014 | Machon ............ A61B 5/6803 600/383 |
| 2014/0268099 A1* | 9/2014 | Moslehi ............ A61B 5/1107 356/32 |
| 2014/0378871 A1* | 12/2014 | Ho .................... G01B 7/18 600/587 |

FOREIGN PATENT DOCUMENTS

| | | |
|---|---|---|
| JP | 2007-178256 | 7/2007 |
| JP | 2007-300112 | 11/2007 |
| JP | 2009-048837 | 3/2009 |
| JP | 2011-505897 | 3/2011 |
| JP | 2012-254210 | 12/2012 |
| JP | 2013-168575 | 8/2013 |
| JP | 2013-172841 A | 9/2013 |
| WO | 2013/151128 | 10/2013 |

OTHER PUBLICATIONS

Takanori Kiyokura et al. "Wearable Laser Blood Flowmeter" NTT Technical Review, pp. 24-27, Nov. 2005.

* cited by examiner

FIG. 7

| PRESSURE SENSOR | x COORDINATE VALUE IN RELATIVE COORDINATE SYSTEM | y COORDINATE VALUE IN RELATIVE COORDINATE SYSTEM |
|---|---|---|
| FIRST PRESSURE SENSOR | x1 | y1 |
| SECOND PRESSURE SENSOR | x2 | y2 |
| ⋮ | ⋮ | ⋮ |
| L-TH PRESSURE SENSOR | xL | yL |

MASSAGE MEASUREMENT APPARATUS AND MASSAGE MEASUREMENT METHOD

BACKGROUND

1. Technical Field

The present disclosure relates to a massage measurement apparatus that measures a characteristic parameter of massage and a massage measurement method for measuring a characteristic parameter of massage.

2. Description of the Related Art

A massage is widely known as a therapy performed such that a skin is kneaded or rubbed with a finger, a palm, or the like. Effects of the massage greatly vary depending on how it is performed. Therefore, there is a need for acquiring details of an effective manner of massage and reproducing the massage. However, it is difficult to objectively determine the strength or the pattern of the massage. Hereinafter, the strength of massage or the pattern thereof or the like will also be referred to generically as characteristic parameters of the massage.

One possible technique to measure the characteristic parameters of the actual massage is disclosed in Japanese Unexamined Patent Application Publication No. 11-118635 (hereinafter, referred to as the conventional technique).

In the conventional technique, a pressure distribution sensor sheet disposed on a display is used to detect what pressure is applied to which position of the sheet. The pressure distribution sensor sheet is brought into direct contact with a part of a skin of interest for which measurement is to be performed to detect a distribution of pressure applied during massage (hereinafter, such a part will be referred as a measurement target part), and massage is performed through the pressure distribution sensor sheet. This makes it possible to detect the pressure applied to the measurement target part during the massage.

SUMMARY

In general, the massage is performed over a rather large area such as a whole back area, a whole face area, or the like. Therefore, to accurately measure the characteristic parameters of the massage using the conventional technique, it is necessary to measure a large number of points in the measurement target part and collect a large number of measurement results, and thus a troublesome process is necessary.

In view of the above, the size of the pressure distribution sensor sheet according to the conventional technique may be increased such that it becomes possible to obtain measurement results for a plurality of measurement target part at a time. However, there is a difference in arrangement of parts of a body (including a face) among individuals, which causes a reduction in accuracy of the measurement result.

That is, it is difficult to easily measure the characteristic parameters of the massage with high accuracy using the conventional technique.

One non-limiting and exemplary embodiment provides a massage measurement apparatus capable of easily measuring a characteristic parameter of massage with high accuracy.

In one general aspect, the techniques disclosed here feature that a massage measurement apparatus includes a sheet member attachable to a skin of a body, and a measurement unit that measures a pressure distribution on the sheet member, wherein the sheet member has an indication that indicates an area of the skin, to which the sheet member is to be attached, and wherein the measurement unit measures the pressure distribution with reference to one or more positions on the body in a state in which the sheet member is attached to the skin.

According to the present disclosure, it is possible to easily measure a characteristic parameters of the massage with high accuracy.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 is a diagram illustrating an example of a correspondence between pressure sensors and their positions according to the second embodiment;

DETAILED DESCRIPTION

Embodiments of the present disclosure are described below in detail with reference to drawings.

First Embodiment

A first embodiment of the present disclosure is an example of a basic aspect of the present disclosure.

Figure 1:
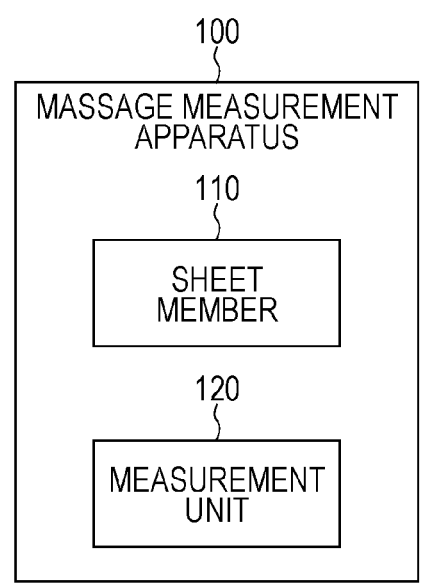
FIG. 1 is a diagram illustrating an example of a structure of a massage measurement apparatus according to a first embodiment of the present disclosure.

FIG. 1 is a block diagram illustrating an example of a structure of the massage measurement apparatus according to the present embodiment.

In FIG. 1, the massage measurement apparatus 100 includes a sheet member 110 and a measurement unit 120.

The sheet member 110 is a member attachable to a skin of a body. The sheet member 110 has an indication representing a skin area to which the sheet member 110 is to be attached. For example, the skin area corresponds to positions of parts of a body (one or more positions on the body).

The measurement unit 120 measures a distribution of pressure applied to the sheet member 110. The measurement unit 120 measures the pressure distribution using positions of parts of the body (one or more positions on the body) as reference positions in a state in which the sheet member 110 is attached to the area described above.

The massage measurement apparatus 100 includes, although not illustrated, for example, a central processing unit (CPU), a storage medium such as a read only memory (ROM) in which a control program is stored, a random access memory (RAM) or the like serving as a work memory, a pressure sensor, and the like. In this configuration, the function of the measurement unit 120 is realized by executing the control program by the CPU.

The massage measurement apparatus 100 configured in the above-described manner allows a massage massage reception person or a massage therapist or a measurement operator to easily attach the sheet member 110 to the skin area to which the sheet member 110 is to be attached. Furthermore, it becomes possible for the massage measurement apparatus 100 to measure the pressure distribution using positions of parts of the body (one or more positions on the body) as reference positions in a state in which the sheet member 110 is attached to the area described above. Thus, the massage measurement apparatus 100 according to the present embodiment is capable of easily measuring the characteristic parameters of the massage with high accuracy.

Second Embodiment

A second embodiment of the present disclosure presents a specific example of an aspect of the present disclosure in which the sheet member is realized in the form of a face sheet that is to be attached to a face. That is, in this example, a face is the area of the body to which the massage is performed.

Appearance and Configuration of Massage Measurement Apparatus

First, a description is given as to an external appearance and a structure of the massage measurement apparatus according to the present embodiment.

Appearance of Massage Measurement Apparatus

Figure 2:
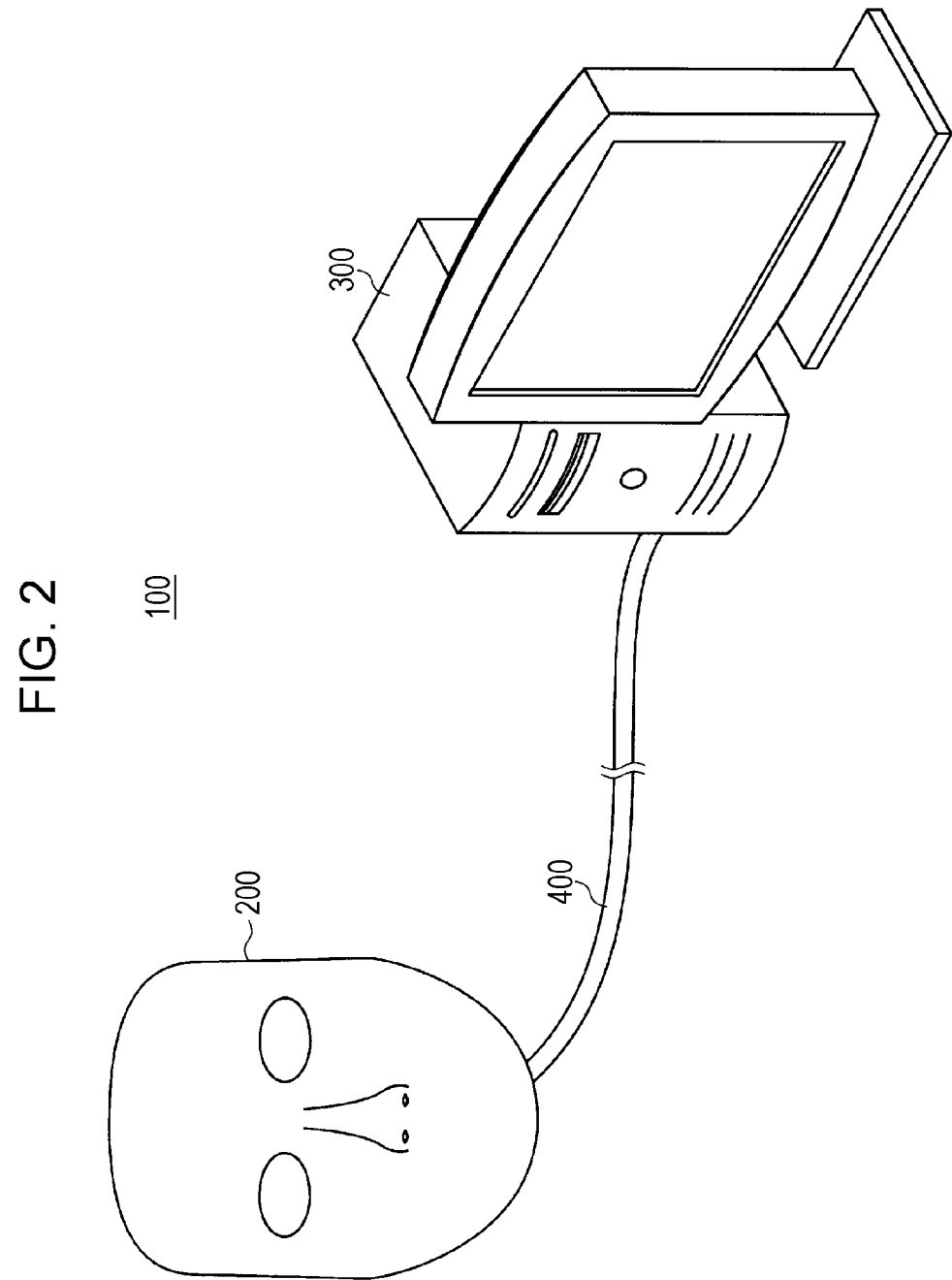
FIG. 2 is a diagram illustrating an example of an external appearance of a massage measurement apparatus according to a second embodiment of the present disclosure.

FIG. 2 is a diagram illustrating an example of the external appearance of the massage measurement apparatus according to the present embodiment.

As illustrated in FIG. 2, the massage measurement apparatus 100 includes a sheet device 200 and a control unit 300.

The sheet device 200 is a device formed in the shape of a sheet capable of three-dimensionally covering the surface of a face and having openings formed at least at locations corresponding to eyes. The sheet device 200 is formed of an elastic sheet member as a main material. As for the sheet member serving as the main material, for example, an energy ray-curable composition material including a polyurethane polymer terminated with an acryloyl group and an acrylic monomer such as that disclosed in Japanese Unexamined Patent Application Publication No. 2013-168575 may be employed.

A specific area of the skin of the body of a massage massage reception person to which the sheet member of the sheet device 200 is to be attached (hereinafter, such an area will be referred to as a target area) is, in this case, an area of a skin of a face excluding at least eye areas.

When the sheet device 200 is attached to the target area of the face, a surface tension allows the sheet device 200 to remain in a state in the sheet device 200 is in intimate contact with the surface of the skin of the face. To ensure sufficiently high adhesion, an adhesive and biocompatible material such as spirit gum, a silicone adhesive, a latex adhesive, or the like may be additionally used.

It is desirable to provide a plurality of sheet devices 200 with different sizes so that it is allowed to select a proper one of the sheet devices 200 depending on a size of a face. Note that the sheet device 200 may have a size slightly smaller than the size of the face to which the sheet device 200 is to be attached. That is, the sheet device 200 is produced assuming that it is expanded in a horizontal or vertical direction when it is attached to the face.

In a state in which the sheet member is attached to the target area, massage is performed on the skin in the target area via the sheet member (that is, via the sheet device 200). It is desirable that the sheet device 200 is sufficiently thin and flexible so as to minimize inhibition against the effects of the massage on the skin. Hereinafter, the massage performed via the sheet member attached to the target area will be referred to simply as massage.

The sheet device 200 includes a plurality of pressure sensors (not illustrated) disposed on a surface of the sheet member that is in direct contact with the face (hereinafter, the surface on this side is referred to as an inner surface. The structure of the sheet device 200 including the pressure sensors and their locations will be described in further detail later.

The control unit 300 may be an information processing apparatus such as a personal computer. The control unit 300 measures the characteristic parameters of the massage by using the plurality of pressure sensors disposed on the sheet device 200. Note that in the present embodiment, information on the characteristic parameters of the massage is information representing how large or small pressures are applied to which parts of the target area during the massage. Hereinafter, the measurement of the characteristic parameters of the massage will also be referred to simply as massage measurement. The control unit 300 is connected to the sheet device 200 via a cable 400.

The cable 400 includes signal lines that connect the control unit 300 to the respective pressure sensors although they are not illustrated in figures.

Structure of Sheet Device

The sheet device 200 includes markers provided on a surface (an outer surface) of the sheet member opposite to the surface that is in direct contact with the face such that the markers represent points whose respective position are to be adjusted with respect to corresponding feature points of the face (hereafter also referred to as face feature points). The points whose respective positions are to be adjusted with respect to the face feature points are located close to the face feature points such as inner eye corners when the sheet device 200 is correctly attached to the target area.

Figure 3:
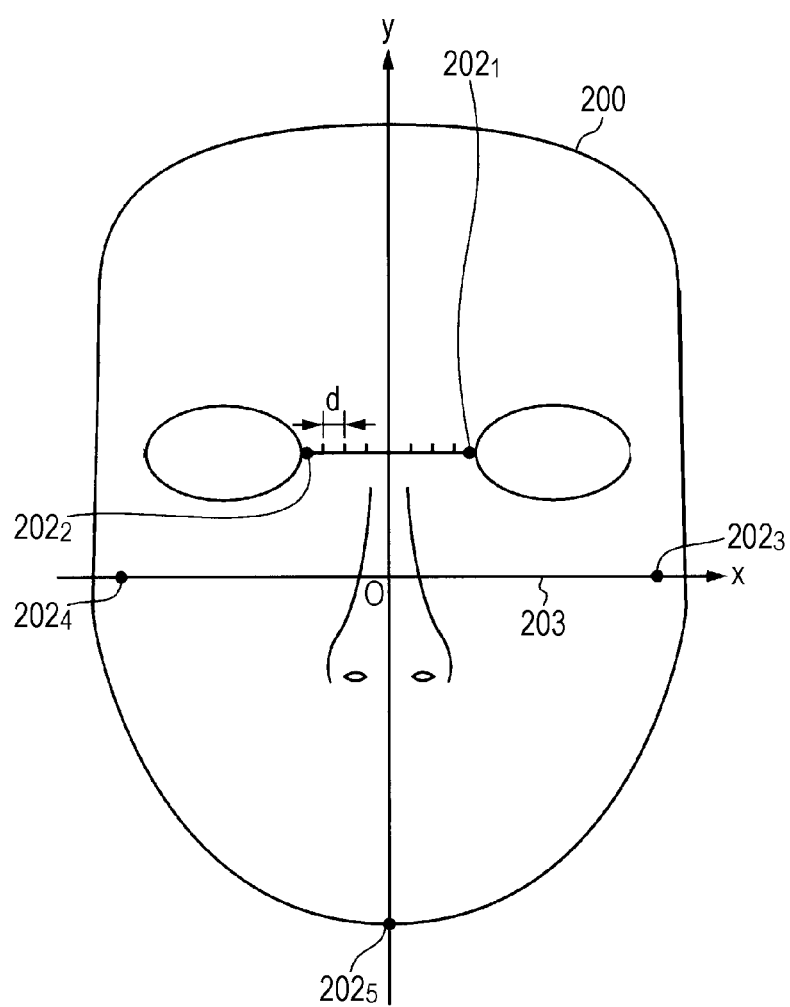
FIG. 3 is a diagram illustrating an example of an arrangement of markers according to the second embodiment.

FIG. 3 is a diagram illustrating an example of an arrangement of markers on the sheet device 200.

As illustrated in FIG. 3, the sheet device 200 includes markers $202_1$, $202_2$, $202_5$, $202_3$, and $202_4$ (denoted by solid dots in FIG. 3) formed at locations corresponding to face feature points, that is, a left inner eye corner, a right inner eye corner, a point of jaw, an apex of a left cheekbone, an apex of a right cheekbone, and the like. That is, the sheet device 200 has markers $202_1$ to $202_5$ serving as position adjust markers thereby making it possible to attach the sheet device 200 correctly to the target area. That is, the markers $202_1$ to $202_5$ indicate the area of the skin (locations of parts of the face) to which the sheet device 200 is to be attached.

For example, a massage massage reception person attaches the sheet device 200 to her/his face while expanding the sheet device 200 such that the respective markers $202_1$ to $202_5$ are located close to the corresponding face feature points. This makes it possible for the massage reception person to attach the sheet device 200 correctly to the target area.

Note that in a case where the sheet device 200 has a shape representing the area of the face to which the sheet device 200 is to be attached to, as in the case of the example illustrated in FIG. 3, the markers are not necessarily needed.

A relative coordinate system 203 for defining the locations of the pressure sensors is set based on a plurality of locations $202_1$ to $202_5$ corresponding to the left inner eye corner, the right inner eye corner, the point of jaw, the apex of the left cheekbone, and the apex of the right cheekbone (the locations are the same as those of the markers in the present embodiment, but the locations are not limited to those in the present example). The relative coordinate system 203 will be described in further detail below.

Figure 4:
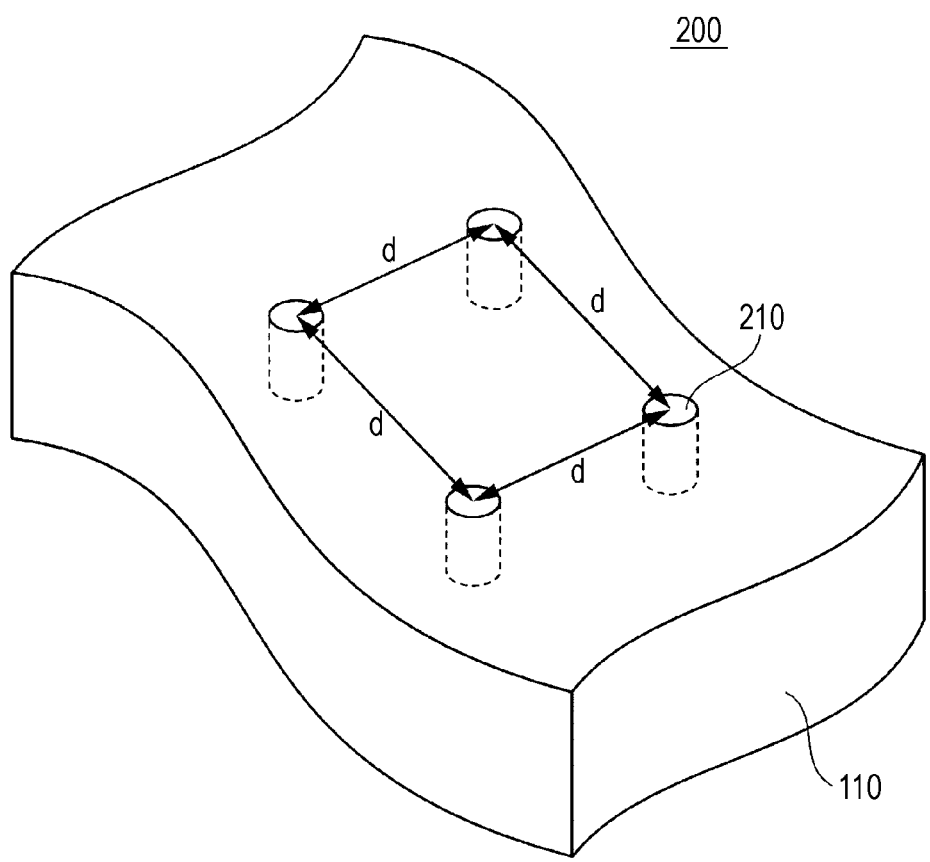
FIG. 4 is a diagram illustrating an example of a structure of a sheet device according to the second embodiment.

FIG. 4 is a diagram illustrating an example of a configuration of a sheet device 200. Note that FIG. 4 illustrates a part of the sheet device 200.

In FIG. 4, the sheet device 200 includes an elastic and thin sheet member 110 and pressure sensors 210 embedded in the sheet member 110.

Each pressure sensor 210 detects a pressure applied to the sheet member 110 in a direction (a vertical direction in FIG. 4) perpendicular to the sheet member 11. That is, when massage is performed in a state in which the sheet device 200 is attached to the skin, the pressure sensors 210 detect pressures applied to respective corresponding parts of the skin.

The pressure sensors 210 are disposed, for example, at intervals of d in a matrix such that one pressure sensor 210 is located in each one of imaginal subareas produced by conceptually dividing a part or all of the sheet member 110 (target area). The length d is, for example, equal to one eighth of the distance between the position $202_1$ corresponding to the and the position $202_2$ corresponding to the right inner eye corner in a state in which the sheet device 200 is not expanded, as illustrated in FIG. 3.

That is, each subarea has its own pressure sensor 210 disposed therein thereby making it possible to measure a pressure applied to the subarea. The each pressure sensor 210 output a measured pressure value.

As for each pressure sensor 210, for example, a pressure sensor realized using an organic thin film transistor disclosed, for example, in Japanese Unexamined Patent Application Publication No. 2007-178256 may be employed. Alternatively, as for each pressure sensor 210, a pressure sensor realized using an organic thin film transistor formed in the shape of a flexible sheet disclosed, for example, in Japanese Unexamined Patent Application Publication No. 2013-168575 may be employed. The organic thin film transistors described above are disposed such that the transistors are connected to a circuit board via conductors formed of a base material having elasticity.

In the present embodiment, the sheet device 200 includes L pressure sensors 210. Note the the number of and locations of pressure sensors 210 are not limited to those in the example illustrated in FIG. 4. The arrangement density of pressure sensors 210 in the sheet device 200 may or may not be uniform.

Structure of Pressure Sensor

Figure 5:
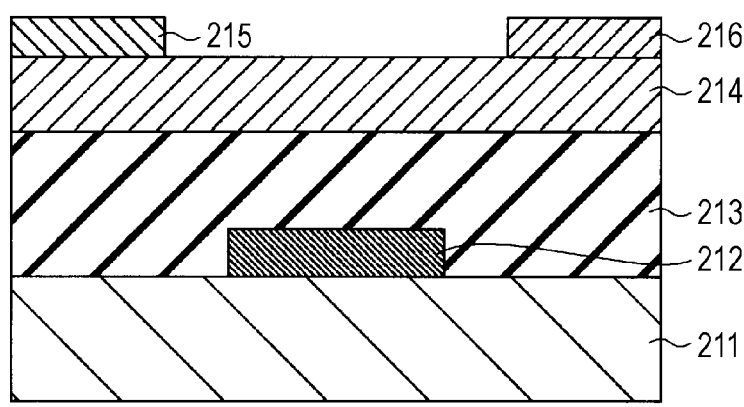
FIG. 5 is a diagram schematically illustrating an example of a structure of a pressure sensor according to the second embodiment.

FIG. 5 is a diagram roughly illustrating an example of a structure of the pressure sensor 210 realized using an organic thin film transistor.

The pressure sensor 210 is formed such that a gate electrode layer 212 is disposed on the surface of an elastic base material 211, and a gate insulator layer 213 and an organic molecular layer 214 are further disposed on the gate electrode layer 212 in a multilayer structure. The elastic base material 211 may be part of the sheet member 110. The pressure sensor 210 further includes a source electrode 215 and a drain electrode 216 that are disposed at spaced-apart locations on an organic molecular layer 214.

The gate insulator layer 213 is formed of a flexible material such as natural rubber, polyisoprene rubber, styrene-butadiene copolymer rubber, polybutadiene rubber, butyl rubber, or the like. The static capacitance between the gate and the source and that between the gate and the drain change depending on the degree of compression of the gate insulator layer 213. By detecting this static capacitance, it is possible to detect the pressure applied to the pressure sensor 210, that is, the pressure applied to the sheet member 110.

Functional Configuration of Massage Measurement Apparatus

Figure 6:
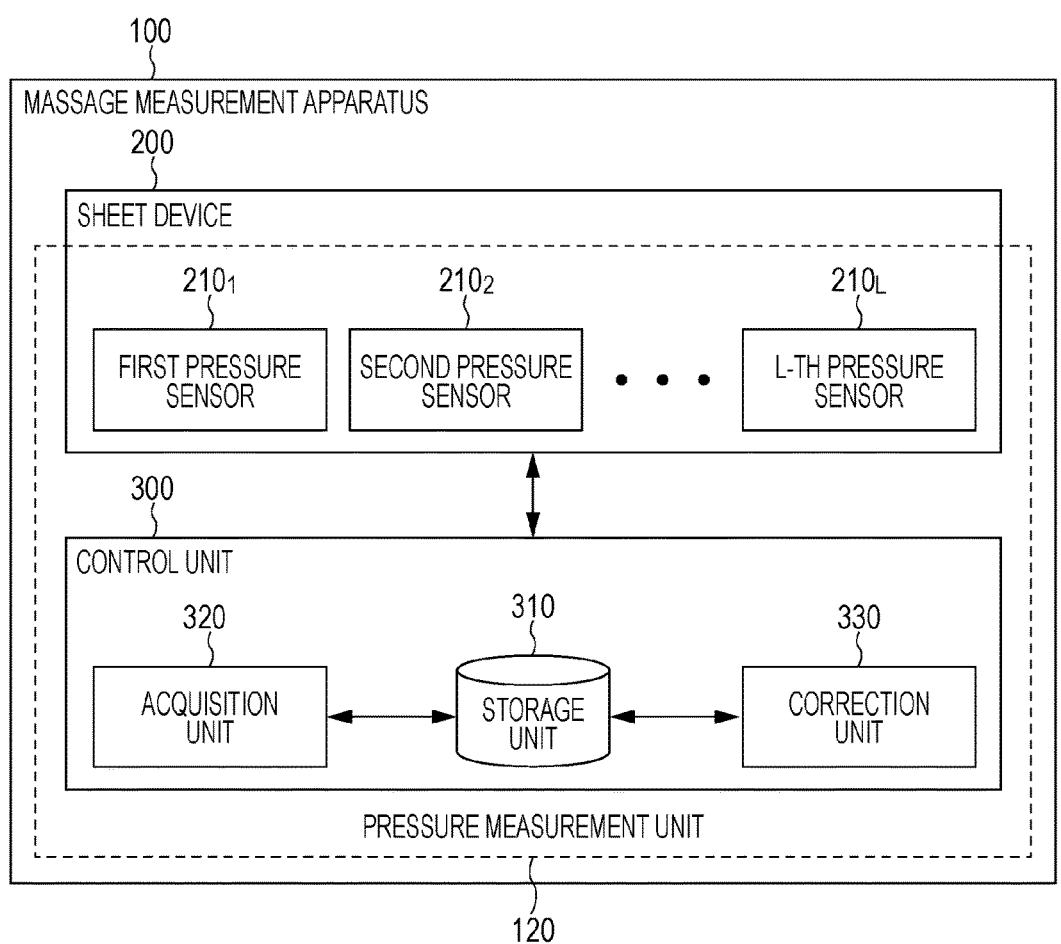
FIG. 6 is a diagram illustrating an example of a functional configuration of a massage measurement apparatus according to the second embodiment.

FIG. 6 is a diagram illustrating an example of a functional configuration of the massage measurement apparatus 100.

In FIG. 6, the massage measurement apparatus 100 includes first to L-th pressure sensors $210_1$ to $210_L$ disposed on the sheet device 200 (see FIG. 2). The massage measurement apparatus 100 further includes a storage unit 310, an acquisition unit 320, and a correction unit 330, all of which are disposed in the control unit 300 (see FIG. 2). Note that the measurement unit 120 of the present disclosure is formed by a combination of the first to L-th pressure sensors $210_1$ to $210_L$, the storage unit 310, the acquisition unit 320, and the correction unit 330.

The storage unit 310 includes, for example, an information storage medium such as a hard disk or the like. The storage unit 310 stores a correspondence relationship between the pressure sensor 210 and its location. The storage unit 310 includes a table representing this correspondence relationship.

Correspondence Relationship Between Pressure Sensor and its Location

FIG. 7 is a diagram illustrating an example of a correspondence relationship between the pressure sensor 210 and its location.

As illustrated in FIG. 7, a correspondence relationship 510 represents a correspondence between identification information 511 of each pressure sensor 210 and the location of the pressure sensor 210 represented by a x coordinate value 512 and a y coordinate value 513 in the relative coordinate system 203 (see FIG. 3). Coordinate values in the relative coordinate system 203 are represented in units of d equal to the pitch of the arrangement of the pressure sensors 210.

The relative coordinate system 203 is, as described above, a coordinate system defined based on a location of a part (one or more parts, such as inner eye corners of right and left eyes, a point of jaw and the like) of a face in a state in which the sheet device 200 is attached to the target area.

For example, the relative coordinate system 203 is set in a plane including positions $202_3$ to $202_5$ (see FIG. 3) respectively corresponding to the point of jaw, the apex of the left cheekbone, and the apex of the right cheekbone, such that an x axis passes through the positions $202_3$ and $202_4$ and a y axis is perpendicular to the x axis and passes through the position $202_5$. The unit of the coordinate value in the relative coordinate system 203 is based on the distance between the left inner eye corner and the right inner eye corner in the plane.

The relative coordinate system 203 defined in the above-described manner is not influenced by a difference in positions of face parts (face feature points) among individuals, and thus use of the relative coordinate system 203 makes it possible to give a spatially normalized expression of the distribution of the pressure applied to the skin during the massage. Thus by using the relative coordinate system 203, it becomes possible to accurately measure the characteristic parameter of massage in such a manner that the measured result is applicable to a face of another person.

Furthermore, by referring to the correspondence relationship 510, it becomes possible to map the pressure values measured by the respective pressure sensors 210 into the relative coordinate system 203.

The storage unit 310 illustrated in FIG. 6 is also used as required by the acquisition unit 320 and the correction unit 330, which will be described later, and various kinds of information such as information representing the measured characteristic parameters of the massage are stored in the storage unit 310. The storage unit 310 preferably includes a frame memory serving as a memory area for storing the pressure values mapped to the relative coordinate system 203.

The acquisition unit 320 is connected to the respective first to L-th pressure sensors $210_1$ to $210_L$ via the cable 400 (see FIG. 2) that connects the control unit 300 to the sheet device 200 and via high-elasticity signal lines (not illustrated) embedded in the sheet device 200. Thus, the acquisition unit 320 is capable of outputting a control signal to each pressure sensor 210 to control the operation of the pressure sensor 210 and is capable of receiving an input of a pressure value output from each pressure sensor 210.

The acquisition unit 320 maps the pressure values output from the respective pressure sensors 210 onto the relative coordinate system 203 (see FIG. 3) while referring to the correspondence relationship 510 (see FIG. 7). The acquisition unit 320 stores a set of mapped pressure values at each time (hereinafter, such a set of values will be referred to as a time-specific pressure value distribution) in the storage unit 310 in relation to information representing the time t at which the pressure values were measured (hereinafter referred to as a measurement time).

The measurement time t represents, for example, a time elapsed since a particular reference time such as a time at which a sequence of massage operations is started. The acquisition unit 320 performs the measurement of the pressure values using the first to L-th pressure sensors $210_1$ to $210_L$ and the mapping thereof at every predetermined time interval dt. Thus, the sequence of time-specific pressure value distributions along the time axis is integrated together on the time axis thereby obtaining information representing the pressure distribution in the massage expressed by a combination of the coordinate values in the relative coordinate system 203 (see FIG. 3), the values along the time axis, and the pressure values. Hereinafter, the sequence of time-specific pressure value distributions is referred to as pressure distribution information.

The correction unit 330 corrects the pressure distribution information representing the result of the measurement by the first to L-th pressure sensors $210_1$ to $210_L$ so as to more accurately characteristic parameter values of the actual massage, and the correction unit 330 stores the corrected pressure distribution information as the final characteristic parameters of the massage.

More specifically, the correction unit 330 corrects each time-specific pressure value distribution stored in the storage unit 310, individually for each level of the pressure value, such that an area corresponding to the level of interest form a closed area having a smooth contour. Hereinafter, this process is referred to as a distribution correction process.

The detection value output from each pressure sensor 210 may include noise caused by a manner of attaching the sheet device 200 to the skin or caused by a detection error. That is, the time-specific pressure value distribution may locally have a pressure value higher or lower than a correct value corresponding to the characteristic parameter of the actual massage. By performing the distribution correction process, it is possible to correct the measurement result so as to obtain characteristic parameter values more accurately representing the actual massage. The distribution correction process will be described in further detail later.

The control unit 300 includes, for example, a CPU, a storage medium such as a ROM in which a control program is stored, and a work memory such as a RAM, although they are not illustrated in the figure. In this case, the function of each part of the control unit 300 is realized by executing the control program by the CPU.

The control unit 300 further includes, although not illustrated, a power supply unit and an operation unit such as a key switch. The power supply unit supplies electric power for operating the CPU and the sheet device 200. The operation unit receives, for example, various operations including an operation for starting the measurement of the massage, performed by a massage therapist or a measurement operator.

By configuring the massage measurement apparatus 100 in the above-described manner, it becomes possible to easily attach the sheet member 110 to the target area, and it becomes possible for the massage measurement apparatus 100 to measure the pressure distribution using the relative coordinate system 203 defined based on the locations of particular parts of the face (one or more positions on the face).

Operation of Massage Measurement Apparatus

Next, an operation of the massage measurement apparatus 100 is described below.

Figure 8:
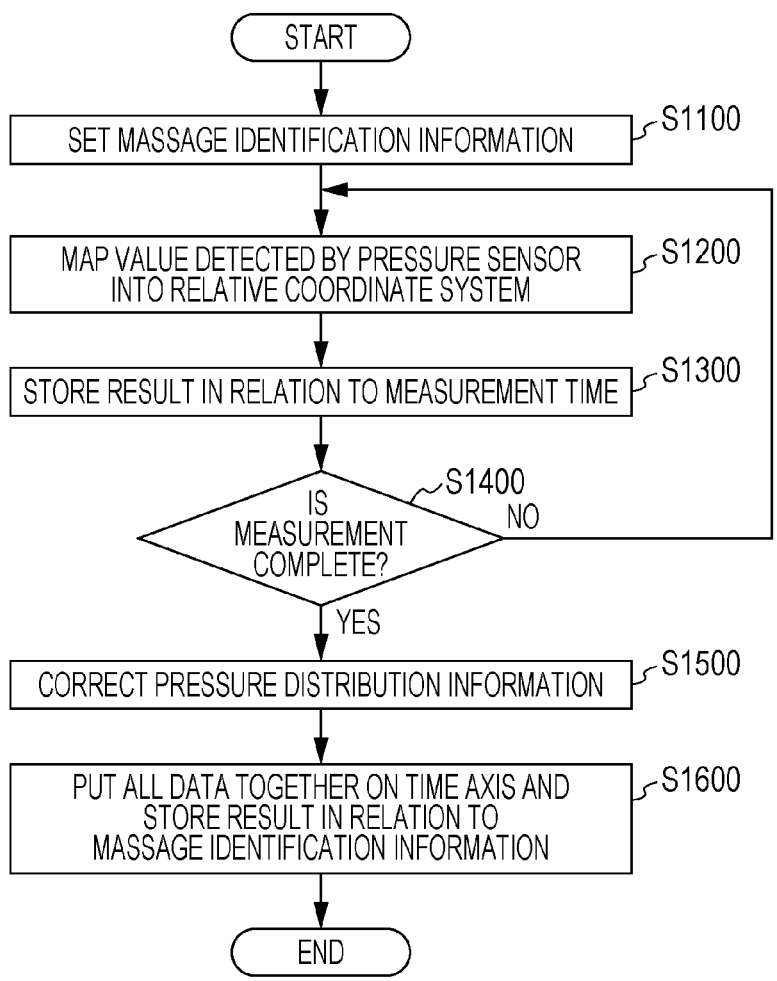
FIG. 8 is a flow chart illustrating an example of an operation of a massage measurement apparatus according to the second embodiment.

FIG. 8 is a flow chart illustrating an example of an operation of the massage measurement apparatus 100.

When a command is issued by a massage therapist or a measurement operator to start the operation in a state in which the sheet device 200 is correctly attached (fitted) to, for example, a target area of a face of a massage reception person, the massage measurement apparatus 100 starts the operation described below.

First, in step S1100, the acquisition unit 320 sets identification information of massage to be measured (hereinafter referred to massage identification information).

The massage identification information includes, for example, a name of a target area, a name of the massage, a name of a massage operator, date, and the like. The massage identification information may further include information about the massage reception person to whom the massage is applied, such as a type of the massage reception person (a body type, an age, a gender, a skin condition, and the like), a body condition of the massage reception person (the degree of shoulder stiffness, the degree of eyestrain, etc.) and/or the like. The acquisition unit 320 receives an input of massage identification information, for example, from the massage therapist or the measurement operator.

In the state in which the sheet device 200 is attached to the target area, there is a possibility that a pressure caused by a tension or the like is detected even when no massage is being performed. In view of the above, the acquisition unit 320 may acquire an initial value of a pressure value from each pressure sensor 210 to make it possible to correct a measurement result obtained later based on the initial value. This makes it possible to measure the characteristic parameter of massage with higher accuracy.

The acquisition unit 320 starts counting, using a timer (not illustrated) or the like, a measurement time t with reference to a time at which the massage is started. The acquisition unit 320 detects a massage start time, for example, by detecting a time at which the pressure value of one of the pressure sensors 210.

In step S1200, the acquisition unit 320 maps the detection value output from each pressure sensor 210 onto a relative coordinate system 203 (see FIG. 3) based on a correspondence relationship 510 (see FIG. 7). That is, the acquisition unit 320 acquires the detection value output each pressure sensor 210 in relation to corresponding coordinate values in the relative coordinate system 203.

In step S1300, the acquisition unit 320 stores the mapping result (pressure value distributions for respective measurement times) in the storage unit 310 in relation to the measurement time t and the massage identification information.

Thereafter, in step S1400, the acquisition unit 320 determines whether a command to end the massage measurement is issued via an operation or the like performed by the massage therapist or the measurement operator. In a case where the acquisition unit 320 determines that the command to end the massage measurement is not issued (No in S1400), the acquisition unit 320 returns the processing flow to step S1200. On the other hand, when the command to end the massage measurement is issued, (Yes in S1400), the acquisition unit 320 advances the processing flow to step S1500.

The acquisition unit 320 may determine that the massage measurement is commanded to be ended when the acquisition unit 320 detects, for example, a continuation of a state for a predetermined period such as 10 seconds in which pressure values measured by pressure sensors 210 are all equal to or lower than a predetermined threshold value.

The acquisition unit 320 repeats the process from step S1200 to step S1400 at time intervals of dt of, for example, 0.02 seconds. As a result, a sequence of time-specific pressure value distributions along the time axis (pressure distribution information) is stored in the storage unit 310. The time interval dt is set to a proper value depending on the type of massage. For example, the time interval dt may be set to a short time for massage including a quick operation such as tapping or the like.

In step S1500, the correction unit 330 corrects the stored time-specific pressure value distribution (pressure distribution information) for each measurement time t. The distribution correction process will be described in further detail later.

In step S1600, the correction unit 330 integrates all time-specific pressure value distributions stored in the storage unit 310 along the time axis. The correction unit 330 stores the resultant integrated time-specific pressure value distributions (pressure distribution information) in relation to the assigned massage identification information in the storage unit 310. Thereafter, the present process is ended.

Via the operation described above, the massage measurement apparatus 100 measures the characteristic parameters of the massage and stores the measured result when massage is performed in a state in which the sheet device 200 is attached to the target area. The pressure distribution information stored in the storage unit 310 is high-precision information representing characteristic parameters of the massage performed during the repetition of the process from step S1200 to step S1400.

Pressure Distribution Information

An example of pressure distribution information obtained via the process from step S1200 to step S1400 is described below.

Herein, let it be assumed that the process from step S1200 to step S1400 has been repeated T times and thus T time-specific pressure value distributions have been obtained as pressure distribution information. Furthermore, let it be assumed that the first to L-th pressure sensors $210_1$ to $210_L$ are located in a $(2N+1) \times (2M+1)$ matrix in the relative coordinate system 203 (see FIG. 3), wherein coordinate values in the relative coordinate system 203 are represented in units of d equal to the pitch of the arrangement of the pressure sensors 210.

Figure 9:
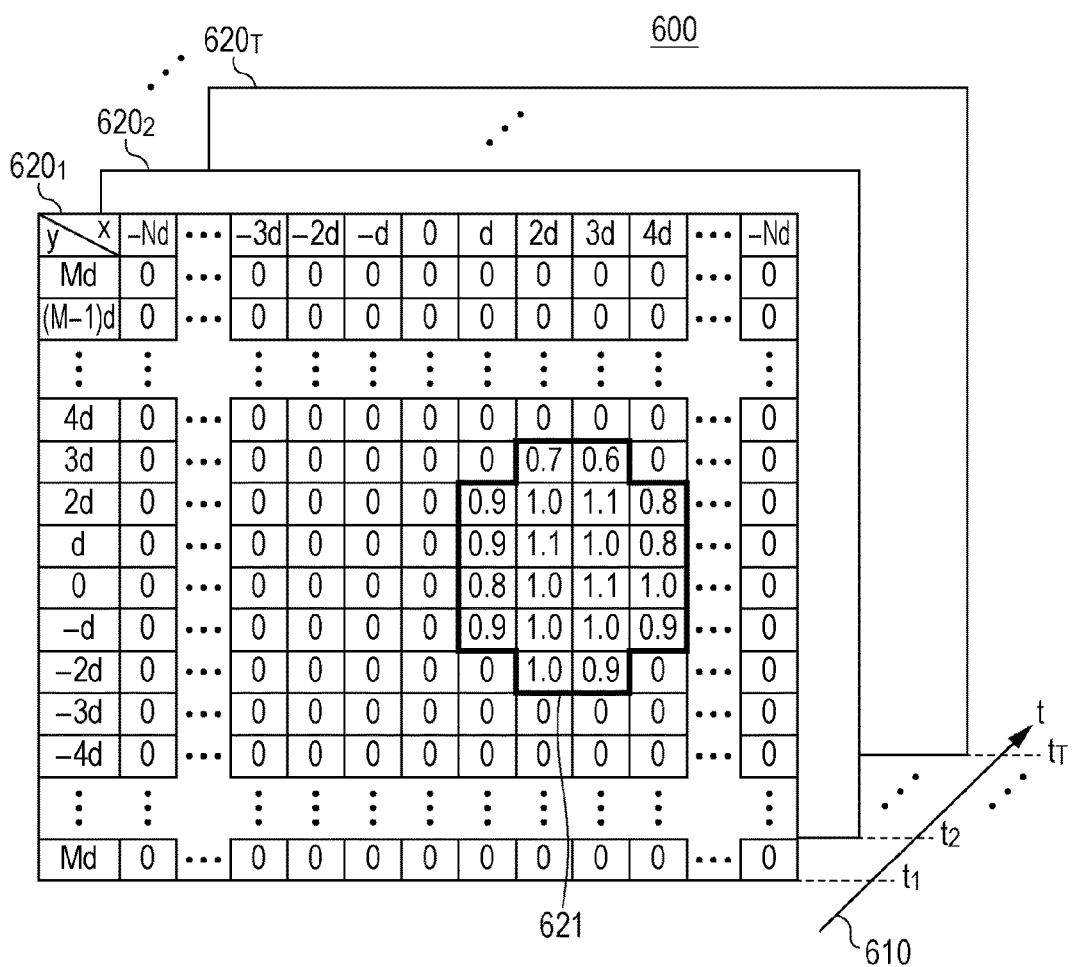
FIG. 9 is a diagram illustrating an example of a set of values representing pressure distribution information according to the second embodiment.

FIG. 9 is a diagram illustrating an example of a characteristic parameter of pressure distribution information stored in the information storage unit 310.

As illustrated in FIG. 9, the pressure distribution information 600 includes time-specific pressure value distributions $620_1$, $620_2$, ..., $620_T$ at times $t_1$, $t_2$, ..., $t_T$ along the time axis 610 of the measurement time t. Each time-specific pressure value distribution 620 includes pressure values measured at a corresponding measurement time t by the respective pressure sensors 210 wherein the pressure values are stored in the $(2N+1) \times (2M+1)$ matrix.

For example, the time-specific pressure value distribution $620_1$ has a high pressure value in a certain area 621. This implies that massage was performed at time t on an area of the skin corresponding to this area 621, for example, by pressing this area of the skin with a finger or the like.

Note that the data format of the pressure distribution information 600 is not limited to that illustrated in FIG. 9.

Figure 10:
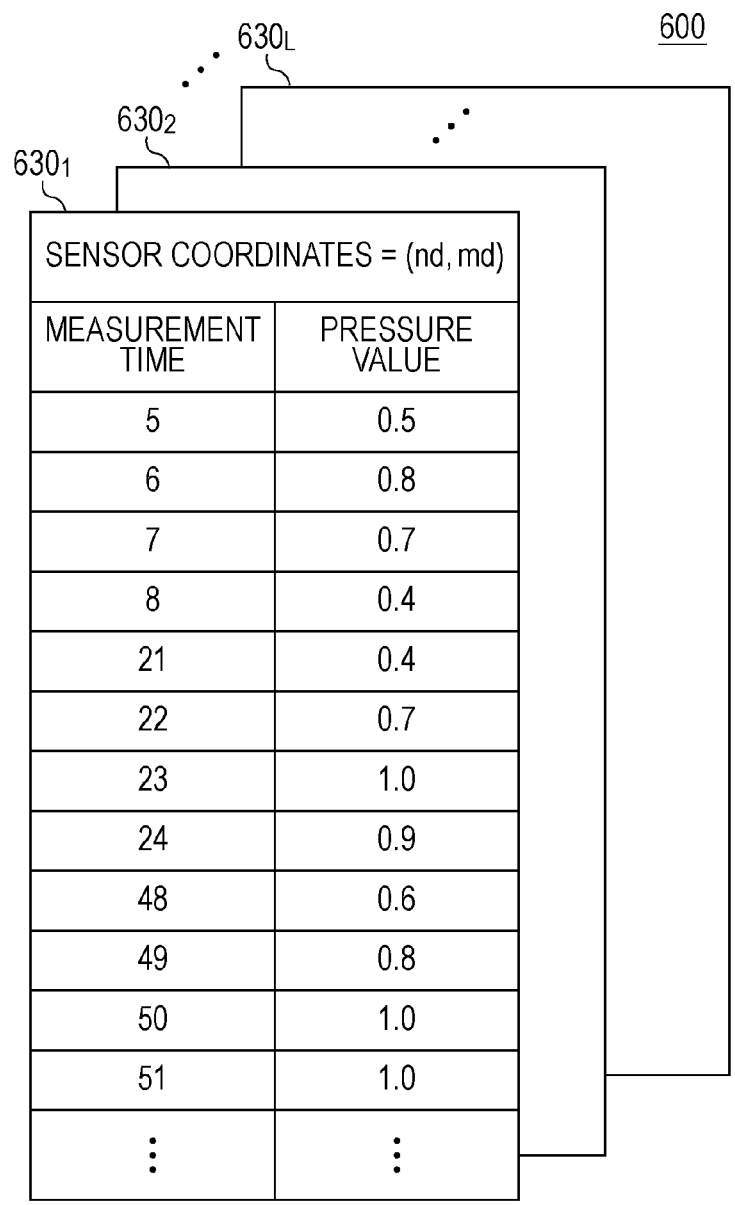
FIG. 10 is a diagram illustrating another example of a set of values representing pressure distribution information according to the second embodiment.

FIG. 10 is a diagram illustrating another example of a characteristic parameter of pressure distribution information stored in the information storage unit 310.

As illustrated in FIG. 10, the pressure distribution information 600 may be described in tables table $630_1$, $630_2$, ..., $630_L$ such that pressure distribution information obtained at coordinate values (sensor coordinates) of the position of each pressure sensor 210 in the relative coordinate system 203 is described in one table and such that each table describes a set of pairs each including a pressure value and time at which the pressure value was measured at the coordinate values.

In the case where the data format illustrated in FIG. 10 is employed, a pressure value that does not need to be stored, such as a pressure value that can be regarded as zero, may not be stored. Therefore, usage of the data format illustrated in FIG. 10 allows a reduction in necessary memory capacity compared with the matrix data format illustrated in FIG. 9. However, in a case where a distribution correction process is performed, the data format illustrated in FIG. 9 may be more preferable.

Distribution Correction Process

Next, an example of a distribution correction process performed in step S1500 is described below.

Figure 11:
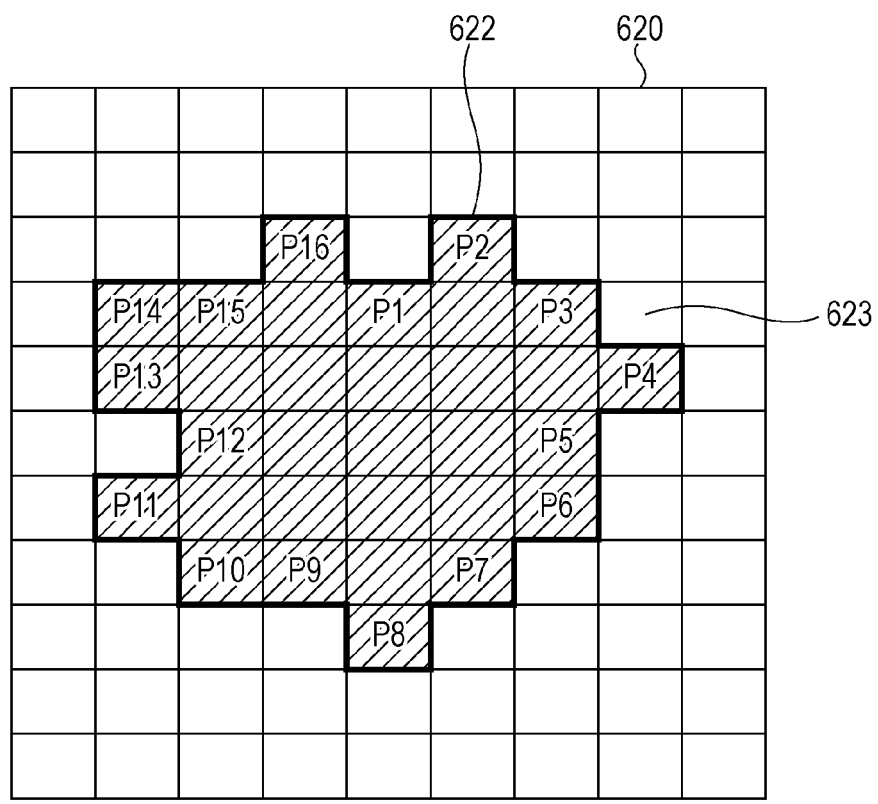
FIG. 11 is a diagram illustrating an example of a time-specific pressure value distribution before a distribution correction process is performed, according to the second embodiment.

FIG. 11 is a diagram illustrating an example of a time-specific pressure value distribution, corresponding to FIG. 9, before the distribution correction process is performed. In FIG. 11, a pressure value in each shaded block is equal to or greater than a predetermined value. Hereinafter, an area in which the pressure value is equal to or greater than the predetermined value is referred to as a high pressure value area, while an area in which the pressure value is lower than the predetermined value is referred to as a low pressure value area.

The massage is performed with a finger or a palm of a massage therapist. Therefore, an actual pressure distribution has a smooth contour, and thus a correct measured pressure distribution must have a smooth contour. On the other hand, detection values output from the respective pressure sensors 210 include noise as described above.

The presence of noise or the like may cause the high pressure value area 622 in the time-specific pressure value distribution 620 to have a rough contour as illustrated in FIG. 11.

In view of the above, the correction unit 330 first extracts, from the high pressure value area 622, subareas adjacent to a low pressure value area 623. The correction unit 330 then assigns ascending numbers i to the pressure values in the extracted subareas (hereinafter referred to as subareas on an area boundary) in order in a clockwise direction. Thereafter, the correction unit 330 replaces the coordinate values $(x_i, y_i)$ of the pressure value of each subarea on the area boundary by coordinate values $(x'_i, y'_i)$ obtained, for example, according to equations (1) and (2) described below. This replacement is performed for all subareas on the area boundary.

$$x'_i = (0.1 \times x_{i-2} + 0.4 \times x_{i-1} + 0.4 \times x_{i+1} + 0.1 \times x_{i+2})/4 \quad (1)$$

$$y'_i = (0.1 \times y_{i-2} + 0.4 \times y_{i-1} + 0.4 \times y_{i+1} + 0.1 \times y_{i+2})/4 \quad (2)$$

The original pressure values at respective locations (coordinate values $(x_i, y_i)$) in the subareas on the area boundary are maintained unless the locations are replaced by other locations.

In a case where as a result of the process described, coordinate values $(x_i, y_i)$ are replaced with other coordinate values $(x'_i, y'_i)$ in a high pressure value area 622, the correction unit 330 corrects a pressure value at the coordinate values $(x_i, y_i)$ by replacing this pressure value with a value (for example, zero) lower than the predetermined level. Conversely, in a case where as a result of the process described above, coordinate values at which the pressure value is less than the predetermined level are surrounded by high pressure value area 622, the correction unit 330 replaces this pressure value at the coordinate values with an average value of pressure values of adjacent subareas in the high pressure value areas 622.

The correction unit 330 performs the above-described distribution correction process for all time-specific pressure value distributions 620 stored in the storage unit 310.

Figure 12:
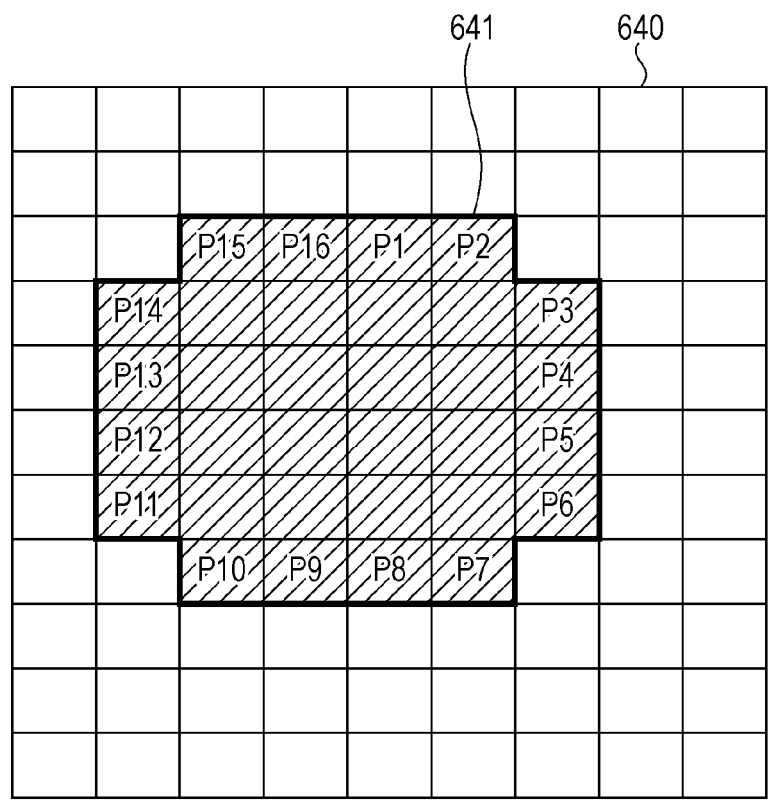
FIG. 12 is a diagram illustrating an example of a time-specific pressure value distribution after the distribution correction process is performed, according to the second embodiment.

FIG. 12 is a diagram illustrating an example of a time-specific pressure value distribution after the distribution correction process is performed on the time-specific pressure value distribution illustrated in FIG. 11.

As illustrated in FIG. 12, in the time-specific pressure value distribution 640 corrected via the distribution correction process, the high pressure value area 641 becomes a closed area having a smooth contour. The corrected time-specific pressure value distribution 640 represents more precisely the characteristic parameter of the actual massage than is represented by the original time-specific pressure value distribution 620 that is not subjected to the distribution correction process (see FIG. 11).

As described above, by performing the distribution correction process, the massage measurement apparatus 100 is capable of measuring and storing the characteristic parameter of massage with further higher accuracy.

The correction unit 330 may preferably perform the distribution correction process individually for each level of a plurality of levels of pressure values.

Note that for a particular type of massage such as cupping massage, pressure distribution information may represent more accurately a characteristic parameter of the actual massage when the distribution correction process is not performed than when the the distribution correction process is performed. Therefore, it is desirable to configure the massage measurement apparatus 100 to be capable of selecting whether to perform the distribution correction process.

Effects of Embodiments

According to the embodiments, as described above, the massage measurement apparatus 100 includes the sheet member 110 having the indication representing the area of a skin to which the sheet member 110 is to be attached, measures the pressure distribution applied to the sheet member 110 using the relative coordinate system defined based on the locations of particular parts of the face (one or more positions on the face).

Thus the massage measurement apparatus 100 is capable of easily measuring what magnitude of the pressure is applied to what part of the face at which timing for a relatively large area without being influenced by a difference in locations of parts (face feature points) of the face among individuals. That is, the massage measurement apparatus 100 is capable of easily measuring the characteristic parameter of the massage with high accuracy.

Modifications of the Embodiments

The relative coordinate system used to represent the pressure distribution is not limited to the example described above. For example, the relative coordinate system may be defined based on positions of other face parts (one or more positions of the face) such as ends of eyebrows, eye tails, or the like. The massage measurement apparatus 100 does not necessarily need to use a relative coordinate system. For example, in a case where a relative position of each pressure sensor 210 with respect to a face feature point is known, the detection value of each pressure sensor 210 may is stored or output in relation with only identification information of each pressure sensor 210. On the other hand, in a case where the target area of massage is limited to a particular area (for example, the target area of massage is not the whole face area but a limited area close to an eye), the relative coordinate system may be defined with respect to one position (for example, a middle point between a left inner eye corner and a right inner eye corner). In this case, only one marker may be provided on the sheet device (for example, a marker may be formed on the sheet device at the middle point between two eyes).

Furthermore, the area (target area) to which the sheet member 110 of the sheet device 200 is attached is not limited to an area of a skin of a face. For example, the target area may be a whole back area, a calf, a feet bottom, or other areas of a skin of a body. Alternatively, the target area may be an area including three ore more feature points, which are common among many general people, of a body.

Furthermore, the massage to be measured is not limited to massage performed by a person with a hand or a finger. That is, the massage measurement apparatus is capable of measuring other types of massage such as massage performed using various kinds of massage tools, massage performed using a massage apparatus such as a massage chair, or the like.

The method of the distribution correction process is not limited to the example described above. For example, the massage measurement apparatus 100 may smooth a pressure value distribution in a plane of a relative coordinate system or along a time axis.

The measurement may be limited to only part of a sequence of massage operation. For example, the massage measurement apparatus 100 may measure only a pressure value distribution at a certain time to acquire a pressure distribution applied to a skin at that time.

The massage measurement apparatus 100 may present information indicating a type of massage to be performed and measured, and/or information that prompts a massage therapist to stop the massage or correct the characteristic parameters of the massage.

For example, it is not very desirable to perform massage excessively. In view of the above, the massage measurement apparatus 100 may monitor the temperature of the skin, the blood flow rate, or the like. If the massage measurement apparatus 100 detects an increase in one of the values to a level beyond a predetermined threshold or detects an increase rate thereof greater than a predetermined threshold value, then the massage measurement apparatus 100 may generate an alarm sound to prompt a massage therapist to stop the massage.

In this case, the sheet device 200 may include a temperature sensor or a blood flowmeter disposed on an inner surface. As for the temperature sensor disposed on the sheet device 200, for example, a temperature sensor disclosed in International Publication No. 2013/151128 may be employed.

As for the blood flowmeter disposed on the sheet device 200, for example, a blood flowmeter disclosed in Kiyokura Takanori, Shinnji Mino, and Junichi Shimada, "Ultrasmall-size Wearable Laser Blood Flowmeter", NTT Technical Review, pp. 25-27, November, 2005 may be employed. The blood flowmeter may be realized using a laser diode and a phototransistor. As for the laser diode, for example, an organic laser diode produced by a printing technique using a high-molecule polymer such as that disclosed in Japanese Unexamined Patent Application Publication No. 2009-48837 may be used. As for the phototransistor, for example, an organic phototransistor realized by a high-molecule thin-film transistor such as that disclosed in Japanese Unexamined Patent Application Publication No. 2007-300112 may be used.

There is no particular restriction on usage of the measured characteristic parameters of the massage. For example, the measured characteristic parameters of the massage may be used to reproduce or analyze the characteristic parameters of the massage.

The massage measurement apparatus 100 may output the obtained pressure distribution information 600 to another apparatus via communication, for example, by uploading it to a server disposed on the Internet.

Part or all of functions of the control unit 300 of the massage measurement apparatus 100 may be provided in an apparatus having other functions such as a portable telephone apparatus or the like.

The functions described above may be provided in a server on a network. That is, one or more functions of the massage measurement apparatus 100 may be realized by a cloud server. In this case, the massage measurement apparatus 100 includes a communication unit for transmitting/receiving information to/from the cloud server that provides the above-described functions.

The massage measurement apparatus according to an aspect of the present disclosure includes the sheet member attachable to a skin of a body, and the measurement unit that measures a pressure distribution on the sheet member, wherein the sheet member has an indication that indicates an area of the skin, to which the sheet member is to be attached, and wherein the measurement unit measures the pressure distribution with reference to one or more positions on the body in a state in which the sheet member is attached to the skin.

In the massage measurement apparatus described above, the sheet member may have, as the indication, a shape representing the area.

In the massage measurement apparatus described above, the sheet member may have, as the indication, a marker indicating a position to be adjusted with respect to a feature point of the body.

In the massage measurement apparatus described above, the sheet member may be elastic and may be capable of being attached to the skin of the body in a state in which the sheet member is expanded.

In the massage measurement apparatus described above, the area to which the sheet member is to be attached may be an area of a skin of a face excluding at least eye areas.

In the massage measurement apparatus described above, the measurement unit may measure the pressure distribution using a relative coordinate system defined with reference to positions of parts of the body (one or more positions on the body) in a state in which the sheet member is attached to the area, wherein the relative coordinate system may be defined with reference to at least a plurality of positions on the face, the plurality of positions respectively corresponding to a left inner eye corner, a right inner eye corner, a point of jaw, an apex of the left cheekbone, and an apex of the right cheekbone.

In the massage measurement apparatus described above, the measurement unit may include a plurality of pressure sensors that are disposed respectively in a plurality of subareas into which a part or all of the sheet member is divided, and that measure pressures applied to the respective subareas.

In the massage measurement apparatus described above, the measurement unit may include a correction unit that corrects the measured pressure distribution such that an area corresponding to each level of pressure forms a closed area having a smooth contour.

In the massage measurement apparatus described above, the pressure distribution may be defined by a combination of coordinate values in a relative coordinate system defined with reference to one or more positions on the body, time, and the pressure, in a state in which the sheet member is attached to the area.

According to an aspect of the present disclosure, a massage measurement method, using a sheet member that is capable of being attached to a skin of a body and that includes an indication indicating an area of the skin, to which the sheet member is to be attached, includes attaching the sheet member to the area of the skin according to the indication, and measuring a pressure distribution with reference to one or more positions on the body in a state in which the sheet member is attached to the skin. The massage measurement method described above may further include correcting the measured pressure distribution such that an area corresponding to each level of pressure forms a closed area having a smooth contour; and storing the corrected pressure distribution as a characteristic parameters of the massage performed on the skin via the sheet member.

Thus the present disclosure provides the massage measurement apparatus and the massage measurement method capable of easily measuring the characteristic parameters of the massage with high accuracy.

What is claimed is:

1. A massage measurement apparatus, comprising:
   a sheet member configured to attach to a target area on a skin of a face; and
   a processor that measures, via a plurality of pressure sensors, a pressure distribution on the sheet member,
   wherein the sheet member has a plurality of indications, each of the plurality of indications indicates a position among a plurality of positions on the target area to which each indicator is to be attached, and each of the plurality of indications being matched with a corresponding position of the target area when the sheet member is attached to the target area, and
   wherein the processor maps the pressure distribution to a relative coordinate system corresponding to the target area when the sheet member is attached to the target area in order to determine a strength and pattern of the massage with high accuracy,
   wherein the relative coordinate system is defined with reference to a set of target indications included in the plurality of indications, each indication of the plurality of indications further indicating an area of the skin of the face at which a pressure sensor is positioned, and the processor mapping each indication of the plurality of indications to the relative coordinate system,
   wherein the set of target indications indicates a position of a point of jaw, a position of an apex of a left cheekbone, and a position of an apex of a right cheekbone, and
   wherein the target area includes the point of the jaw, the apex of the left cheekbone, and the apex of the right cheekbone.

2. The massage measurement apparatus according to claim 1, wherein the sheet member has, as the target indications, a shape representing the target area.

3. The massage measurement apparatus according to claim 1, wherein the sheet member has, as the target indications, a marker indicating a position to be adjusted with respect to a feature point of the face.

4. The massage measurement apparatus according to claim 1, wherein the sheet member is elastic and is configured to attach to the skin of the face in a state in which the sheet member is expanded.

5. The massage measurement apparatus according to claim 1, wherein the target area to which the sheet member is to be attached is an area of the skin of a face excluding at least eye areas.

6. The massage measurement apparatus according to claim 1, wherein the processor controls the plurality of pressure sensors that are disposed respectively in a plurality of subareas, into which a part or all of the sheet member is divided, and that measure pressures applied to the respective subareas.

7. The massage measurement apparatus according to claim 1, wherein the processor corrects the measured pressure distribution such that an area corresponding to each level of pressure forms a closed area having a smooth contour.

8. The massage measurement apparatus according to claim 1, wherein the pressure distribution is defined by a combination of coordinate values in the relative coordinate system, time, and the pressure, in a state in which the sheet member is attached to the target area.

9. A massage measurement method using a sheet member that is configured to attach to a skin of a face and that includes a plurality of indications, each of the plurality of indications indicating a position among a plurality of positions on the target area to which each indicator is to be attached, and each of the plurality of indications being matched with a corresponding position of the target area when the sheet member is attached to the target area, the method comprising:
   attaching the sheet member to the target area of the skin according to the plurality of indications;
   massaging the target area by applying pressure on the target area via the sheet member; and
   mapping, by a processor using a plurality of pressure sensors, a pressure distribution with reference to a relative coordinate system corresponding to the target area when the sheet member is attached to the target area in order to determine a strength and pattern of the massage with high accuracy,
   wherein the relative coordinate system is defined with reference to a set of target indications included in the plurality of indications, each indication of the plurality of indications further indicating an area of the skin of the face at which a pressure sensor is positioned, and the processor mapping each indication of the plurality of indications to the relative coordinate system,
   wherein the set of the target indications indicates a position of a point of jaw, a position of an apex of a left cheekbone, and a position of an apex of a right cheekbone, and
   wherein the target area includes the point of the jaw, the apex of the left cheekbone, and the apex of the right cheekbone.

10. The massage measurement method according to claim 9, further comprising:
    correcting the measured pressure distribution such that an area corresponding to each level of pressure forms a closed area having a smooth contour; and
    storing the corrected pressure distribution as characteristic parameters of the massage performed on the target area via the sheet member.

* * * * *